United States Patent [19]
Franklin

[11] Patent Number: 5,977,186
[45] Date of Patent: Nov. 2, 1999

[54] TERPENE TREATMENTS FOR KILLING LICE AND LICE EGGS

[75] Inventor: Lanny Udell Franklin, Atlanta, Ga.

[73] Assignee: XiMed Group PLC, Didcot, United Kingdom

[21] Appl. No.: 09/151,973

[22] Filed: Sep. 11, 1998

Related U.S. Application Data

[60] Provisional application No. 60/072,775, Jan. 27, 1998.

[51] Int. Cl.$^6$ .......................... A01N 27/00; A01N 31/02; A01N 31/08; A01N 35/02
[52] U.S. Cl. .......................... 514/690; 514/733; 514/739; 514/762; 514/763; 514/875; 514/880; 514/881; 510/382; 510/386
[58] Field of Search .......................... 514/690, 739, 514/763, 733, 762, 875, 880, 881, 919; 510/382, 386

[56] References Cited

U.S. PATENT DOCUMENTS

| | | | |
|---|---|---|---|
| 4,927,813 | 5/1990 | Bernstein | 514/65 |
| 4,933,371 | 6/1990 | Hink et al. | 514/739 |
| 5,411,992 | 5/1995 | Eini et al. | 514/731 |
| 5,591,435 | 1/1997 | Vaccarello-Dunkel et al. | 424/195.1 |
| 5,627,166 | 5/1997 | Iwasaki | 514/78 |
| 5,635,174 | 6/1997 | Warren et al. | 424/84 |
| 5,653,991 | 8/1997 | Rod | 424/406 |
| B1 4,379,168 | 1/1990 | Dotolo | 514/763 |

OTHER PUBLICATIONS

BMJ 1995 Nov. 18; 311 (7016):1369; discussion 1369–70. Comment in: BMJ 1996 Jan. 13; 312 (7023); discussion 123.
Vander Stichele R.H. et al. Systematic review of clinical efficacy of topical treatment for head lice. BMJ Sep. 2, 1995. p604–8.

*Primary Examiner*—John Pak
*Attorney, Agent, or Firm*—Tilton, Fallon, Lungmus & Chestnut

[57] ABSTRACT

Treatments are disclosed which comprise formulations of one or more terpenes in aqueous solutions. No resistance to the formulation of the invention has been seen. When used on the scalp or body no extended dwell time is required. The formulations do not have unpleasant odors associated with prior art shampoo treatments for lice and are preferable on grounds of safety to neurotoxins, which are the usual active ingredients associated with prior art treatments. The formulations are directed towards providing topical preparations which may be used on the scalp and hairy body parts, a spray for use on fabrics, a dipping solution for combs and a laundry additive.

26 Claims, No Drawings

TERPENE TREATMENTS FOR KILLING LICE AND LICE EGGS

REFERENCE TO RELATED APPLICATIONS

This application is entitled to the benefit of the filing date of Provisional Application No. 60/072,775, filed Jan. 27, 1998.

FIELD OF THE INVENTION

Pediculosis (lice infestation) in humans has been known since ancient times. Lice infestations are common throughout the world. In the United States alone an estimated ten million cases of pediculosis occurred during 1985 and the numbers have increased substantially since then. In Europe, lice infestation has reached epidemic proportions.

Three types of lice infest humans: 1) head lice, 2) body lice and 3) crab or pubic lice. All are members of the family Pediculidae and most are species within the genus Pediculus. They are small, flat, greyish-black, wingless insects. Their six legs are short and stout, with a large claw on each leg for grasping and holding onto hair. They have piercing and sucking mouth parts for blood feeding and require close contact with human hosts, to which they are very well adapted. The three types differ considerably in habitat and to a small degree, in their life cycles.

The invention is a group of pharmaceutical formulations comprising one or more terpenes which have been found to be effective, in aqueous solutions, in killing lice and their eggs.

BACKGROUND TO THE PRESENT INVENTION AND THE PRIOR ART

Terpenes are bio-active compounds and there are numerous reports in the literature concerning their effects as antibacterial, antifungal, antihelminthic and antimitotic agents. Various terpenes are used in agriculture for growth inhibition, growth promotion and in the food industry as flavourings and fragrances. Interest in the potential for using terpenes in medical applications is increasing.

Lice have three stages in their lift cycle: egg, nymph (young), and adult. Newly hatched nymphs are identical in appearance to their parents except for the 2nd instar (nymph) which is smaller and has undeveloped reproductive organs. Nymphs gradually develop into adults, periodically shedding their skin (moulting) during the process. The life cycle (egg to egg) takes approximately 15 to 35 days during which time a female may lay between 50 and 150 eggs. Lice spend their entire life as ectoparasites on humans and, unlike other insects, they have a relatively consistent environment. Their close contact with human skin ensures favourable temperatures of 82° F. to 86° F., and an abundant food supply. Lice do not abandon their hosts unless the body temperature substantially changes due to death or high fever. Once dislodged from a person's body or clothing, they will infest a new human host in the immediate proximity. If a new host is not found within one to eight days, lice will starve to death.

During feeding, lice inject saliva into the skin of the host and this causes irritation and subsequent itching. Children under 12 years are more sensitive to louse feeding than other age groups. Scratching louse bite areas frequently causes an abrasion, which may become infected with other microorganisms. Prolonged louse infestation causes a hardening and pigmentation of the skin known as "vagabond's disease".

Even though people experience unpleasant sensations as a result of louse infestation, they often deny pediculosis because of feelings of disgust and shame. Lice infestation used to be thought of as a problem only of the poor or poorly housed. It is now abundantly clear that the problem of head lice has extended to very large number of middle class homes in the western world and this leads to increasing numbers of consultations with family practitioners or pharmacists who advise as to the treatment currently being recommended.

Lice are spread through sharing contaminated clothing, hats, scarves, combs, hair brushes, and other headgear, or as a result of close physical contact with an infected person. Other occasional sources are bedding, furniture, rugs and floor surfaces where dislodged lice may be present.

Once infested, an individual usually carries a few dozen lice. However, some people have been known to carry several hundred lice and on rare occasions, one to two thousand lice. Human lice do not normally infest pets and domestic animals.

Of the three species of lice, only body lice have been known to transmit disease organisms. Relapsing fever, typhus, and trench fevers were transmitted by body lice in Europe during World Wars 1 and 2 and the Naples Typhus Epidemic of 1944 was brought under control using DDT to kill lice—one of the earliest widespread uses of this insecticide.

Head lice (*Pediculosus humanus capitus*), are by far the most common and troublesome of the human lice infestations and in the US, alone, between 8 and 12 million children have head lice at any one time.

"Nits" is the term used to describe the small yellowish-white, oval-shaped eggs cases of head lice that are 'glued' at an angle to the side of a hair shaft near its base. Favourite sites are behind the ears or on the nape of the neck. Eggs are laid by a mature female louse and after hatching; feeding starts immediately; this activity causes the young head lice to rapidly develop a reddish-brown colour. Development takes about 18–20 days and the adult can live for about one month, during which time each female lays between 50 and 150 eggs at the rate of 4 to 6 per day, usually at night. The eggs are cylindrical, yellowish-white, and about 0.8 mm long. Feeding occurs at fairly frequent intervals and at least twice daily. The adult male is about 2.1 mm long and the female rather larger, about 3 mm long. Mating occurs within 10 hours of maturation and recurs quite frequently during the remainder of life. Head lice can survive three to four days if dislodged from the host.

Head lice are transferred from one infected person to another through physical contact and the communal use of combs, hair brushes, head apparel, towels, bedding, and personal clothing.

Feeding activity irritates the scalp, causing intense itching. Head lice are not known to transmit any disease organisms directly but a secondary infection may result if the skin is broken by repeatedly scratching the area. In severe infestations the hair may become matted as a result of exudates from louse bites.

The impact of being publicly identified as having lice (for instance in a school classroom) can be distressing and socially embarrassing. Children, particularly those of primary/first school age, are most likely to get head lice because of their close contact and social interactions with each other which creates numerous opportunities for lice to be spread amongst them. Children who become infested in school will carry lice home and may infest family members who unknowingly become a source for recurring louse problems in the home. Few parents react with total equanimity to the discovery.

The body louse or cootie (*Pediculosus humanus humanus*), is very similar to the head louse in physical appearance except that it is 10%–20% percent larger. This insect is generally associated with unclean environments where inadequate bathing occurs or clothes are shared. The body louse lives on clothing that comes in close contact with the human body, such as the waistline and crotch of trousers, shirt armpits and collars and underwear, rather than the body itself which it visits only to obtain a blood meal.

The life cycle of the body louse is, in many respects, similar to that of the head louse. However, in this louse, the fertilised female adult lays nine to ten eggs per day, and may lay 270 to 300 eggs in her lifetime. The eggs are usually glued to fibres of clothing, often in the seams. Eggs hatch in six to nine days. Newly hatched nymphs begin to suck blood at once and feed frequently during day or night, especially when the host is quiet. Nymphs mature to adults in approximately 16 to 18 days, during which process three moultings occur. Newly emerged adult males, 2.3 mm long, and females, 4.2 mm long, mate within a day. The female begins laying eggs one or two days after reaching maturity. The life cycle (egg to egg) is completed in 22 to 28 days. The adults are greyish white, and live approximately 30 to 40 days. After discontinued contact with the host, body lice can survive 8 to 10 days. They spread through contact with infested persons or their clothing.

This crab or pubic louse has a crab-like appearance and is greyish white. Although formerly grouped within the genus Pediculus they are now more correctly classified as *Pthirus pubis* (syn. *Pediculus pubis*). They infest the pubic region of the body but in severe infestations may be found in armpits, moustaches, beards, eyelashes and eyebrows.

Fertilised adult females lay three eggs per day and a total of 26 eggs in their lifetime. The oval, whitish eggs, 1/50 inch long, are glued to coarser hair near the skin. The eggs hatch after six to eight days. The newly hatched nymphs start sucking blood immediately. The nymphs grow into adults after moulting three times in 15 to 17 days. The life cycle (egg to egg) is completed in 34 to 41 days. The adults are 1.6 mm long and live for a month on the human host. If they are dislodged, they survive less than 24 hours.

Both nymphs and adults tend to settle on one spot, and feeding continues intermittently for hours or days. Spread is through intimate physical contact, particularly sexual contact and possibly also through infested bedding, clothing and toilet seats.

In theory, elimination of head lice in an infested family should be relatively straightforward. Advice is readily available in schools and GP surgeries in Western countries. Reporting to school authorities is strongly encouraged but many parents evade the issue because of shame or embarrassment. Failure to report, coupled with lack of awareness that the problem exists or reluctance to deal with it at all, are the primary reasons for reinfestation in the school and community environments. Trained school staff, especially a nurse if there is one, do carry out inspections but often encounter difficulties with parents who adopt a state of denial.

The extent of delousing activities in a school depends on a variety of factors such as the age of the students and general resources. Difficult schools in inner city areas are particularly prone to the problem and have, in general, the least resources and also the least co-operative parent population. It is rare for schools, other than some residential schools, to treat head lice infestation actively. Once infestation is recognised in a group, the classic steps are to encourage inspection of the whole group and all of their family members, to encourage higher standards of personal hygiene and to institute pesticide treatment with chemicals. This tends to be applied as a lotion or conditioner which must be left for a specified dwell-time to be effective. The use of special combs which can remove both live lice and their eggs is also encouraged. The action of combing correctly is considered to help the problem by breaking the legs of the lice. It is also being recommended that hair is over-conditioned with a standard product as this makes it difficult for the lice to grip the hair shaft. In the case of pubic lice, transmitted by sexual contact, it is particularly important that the sexual partner(s) should be treated simultaneously to avoid reinfestation.

Other general recommendations include machine washing in hot water (over 54° C.) or dry cleaning all clothing, including coats, hats, scarfs, pillow cases, towels, and bedding materials, which may have contacted an infested individual.

Most mediated shampoos and lotions for treating head lice are available over the counter, through some require a prescription. Widely used products in the OTC category in the USA include Rid® Lice Killing Shampoo (Pfizer), Nix® Creme Rinse and A-2000® Shampoo Concentrate which contains pyrethrins and piperonyl butoxide as the active ingredients (AI).

Prescribable US brands include Kwell®, (containing lindane 1%, as the active) and Ovidem®, (active ingredient 0.5% malathion).

In the U.K. the treatments for lice have recently received negative press at tention (Sunday Times Oct. 5, 1997 and World In Action, documentary TV programme, Channel 3, Independent TeleVision) and despite the fact that the press focussed on malathion (Derbac-M™, Prioderm™ and Suleo-M™; marketed in the UK by Seton Healthcare) there has been a knock-on effect and lice products generally are being increasingly thought of with caution. The key concerns are regarding the use of organo phosphates and their associated toxicity, especially as they are so often used in young children. Malathion toxicity includes nausea, vomiting, diarrhoea, broncho-constriction, blurred vision, excessive salivation, muscle twitching, cyanosis, convulsions, coma and respiratory failure. Against this background it may be somewhat surprising that its topical use was not more closely monitored earlier. Even permethrin (the active in Lyclear™) has to be used with caution and must not be used in an enclosed space. It must also be kept away from pets and fish of known direct toxicity in those species.

Pediculicides, selectively kill lice which invade the epidermis. Although a number of brands contain either carbaryl or malathion, lotions containing phenothrin and permethrin and now the major products. These are pyrethroid compounds and are highly effective insecticidal neurotoxins, with efficacy against both adult lice and their eggs. Permethrin (3-phenoxyphenyl) methyl (+/−) cis/trans 3-(2,2-dichloroethenyl) 2,2-dimethylcyclopropanecarboxylate, is used as a 0.5% preparation in a paraffin base. Other actives are benzyl benzoate and crotamiton. All are applied topically. The manufactures claim appropriate use does not lead to resistance but evidence now to hand would seem to suggest otherwise. Indeed, local UK Health Authorities (through directives issued to GPs, school nurses and health visitors) advise alternation of products within a co-ordinated national policy. Many Health Authorities are now advising no active treatment because of problems apparently due to resistant lice. Instead they recommend over-conditioning the hair and regular use of a specially designed lice comb.

The main brands used in the U. K. are Lyclear™ Crème Rinse Warner Lambert—a lotion conditioner applied after shampooing and left for 10 minutes and Full Marks™ (phenothrin) Seton Healthcare a lotion rubbed into the hair and left for 2 hours. These 2 products are prescribable but also available over-the-counter. Lyclear™ appears to be the clear market leader. All prior art anti-head lice preparations have the drawback of requiring significant dwell-times on the scalp and this is negative for the products because it reduces user-compliance and encourages misuses. Both tendencies reduce the success rate in clearing lice. Manufacturers claim that resistance is not an issue and that treatment failures are due to incorrect use. However, this does clearly indicate that these agents are not user friendly.

The issue of efficacy of prior art preparations, used to control head lice, is important and in this context, a report by Vander Stichele R. H. et al, from the Heymans Institute of Pharmacology, University of Ghent, Belgium entitled 'Systematic review of clinical efficacy of topical treatments for head lice.' (BMJ Sep. 2, 1995. p604–8), is relevant. The group sought to collect and evaluate all trials on clinical efficacy of topical treatments for head lice. They undertook a systematic review of randomised trials identified from the data sources Medline, International Pharmaceutical Abstracts, Science Citation Index, letters to key authors and companies and hand search of journals. All the trials reviewed were carried out in schools or communities in patients infested with lice. The main outcome measure, which the Review Group were concerned with, was cure rate (absence of live lice and viable nits) on day 14 after treatment. A total of 28 trials were identified and evaluated according to eight general and 18 lice-specific criteria. Of the 14 trials rated as having low to moderate risk of bias, seven were selected because they used the main outcome measure. These seven trials described 21 evaluations of eight different compounds and placebo (all but two evaluations were of single applications). Only permethrin 1% creme rinse showed efficacy in more than two studies with the lower 95% confidence limit of cure rate above 90%. The authors' conclusion was that "only for permethrin has sufficient evidence been published to show efficacy. Less expensive treatments such as malathion and carbaryl need more evidence of efficacy. Lindane (1,2,3,4,5,6-Hexachlorocyclohexane) and the natural pyrethrines are not sufficiently effective to justify their use". In addition, many health authorities and registration agencies regard lindane, which is used as a scabicide, pediculicide and insecticide, as dangerous.

It is tempting to speculate that the mechanism of resistance might be similar to that which arise with certain bacteria—a sub-lethal dose is repeatedly administered and engenders acquired resistance.

In the USA there are also products available for treating bedding, clothing and furniture including Lice Treatment Kit™ (active ingredient: resmethrin 0.5%), R & C Spray™ (active ingredient: phenothrin 0.382%) and Rid® Lice Control Spray (active ingredient: permethrin 0.5%). These products are available from stores rather than pharmacies and so far as is known, there are no equivalent products available in the UK.

Thus there is a significant need for a treatment for this widespread and troublesome problem which would address the issues which detract from the prior art products. An ideal product might offer no dwell time in excess of that for ordinary shampoos used by non-infested individuals, absence of toxicity, user friendly presentation and resistance-free mode of action.

The following US patents are considered relevant:

U.S. Pat. No. 5,635,174; U.S. Pat. No. 4,927,813; U.S. Pat. No. 4,379,168; U.S. Pat. No. 5,411,992; U.S. Pat. No. 5,591,435; U.S. Pat. No. 4,933,371; U.S. Pat. No. 5,627,166.

Other documents considered relevant are:

BMJ Nov. 18, 1995; 311(7016):1369; discussion 1369–70

Comment in: BMJ Jan. 13, 1996;312 (7023): discussion 123.

Co-operative Extension, Institute of Agriculture and Natural Resources, University of Nebraska, Lincoln, Larousse Encyclopaedia of Animal Life Vander Stichele R. H. et al. Systematic review of clinical efficacy of topical treatment for head lice. BMJ Sep. 2, 1995. p604–8.

OUTLINE OF THE PRESENT INVENTION

The present invention comprises formulations for killing lice and lice eggs which may optionally be presented, non-exhaustively, as shampoo for use on the hair or other hairy body parts, a spray for the treatment of fabrics including infested bedding and upholstery, a dipping solution for the immersion of combs which are used by more than one person and an additive for use during washing of infested fabrics in a washing machine or other vessel.

The shampoo is user friendly compared to prior art products which require to be left on the hair for extended periods, referred to by those skilled in the art as 'dwell time'. Other presentations are used for spraying infested fabrics such as bedding and upholstery and as a laundry additive; both are intended to kill lice and eggs. To date the present author has been unable to find any other dip based on any chemical formulation which is specifically intended for brushes and combs to providing a means for preventing reinfection by killing lice and lice eggs on such items.

The active ingredients which are employed in the instant invention are one or more terpenes, preferably those which are naturally occurring and generally unmodified. The preferred terpenes are classified as GRAS (Generally Regarded as Safe) by the Environmental Protection Agency in the USA and have been used for many years in the flavour and fragrance industries.

Certain of the preferred individual terpenes employed in the instant invention are highly effective against both lice and lice eggs and it is considered extremely unlikely that resistance can develop, due to their mode of action. Unlike most other pediculocides, the terpenes used in the instant invention are not neurotoxins.

The shampoo formulation is mild, has a slightly basic pH and has only a slight odour which does not linger on the washed hair. It also preferably contains one or more conditioning agents so that no separate conditioning is necessary. Overall, the product is safe and pleasant to use and is generally acceptable for children, the major end-users for a treatment for head lice. The comb dip and spray products may be based on the shampoo formulation using a lower concentration of the active terpene or terpene combination. The laundry additive product is also based on the shampoo formulation with the addition of a surfactant, preferably though not necessarily, a non ionic surfactant.

DETAILED DESCRIPTION OF THE PRESENT INVENTION

The present invention is a series of pediculocidal formulations containing one or more terpenes. Optimally these include:

Redistilled limonene
Beta-ionone
Linalool
Geraniol
Eugenol
Myrcene
Carvone.

The rationale for the individual constituents and their use in combination is as follows:

Limonene is a powerful pediculocide and I have confirmed this against several species of lice. In the present invention series limonene is used as an adjuvant to enhance the properties of other terpenes. The redistilled version is strongly preferred because it has a low-odour compared with natural d-limonene which has a very strong citrus smell and soon oxidizes, producing an unpleasant aldehyde odour. Redistilled limonene is also more stable than natural d-limonene.

Beta-ionone is an effective pediculicide which also has significant anti-bacterial and anti-fungal properties. In head lice infestation, especially in children, lice feeding sites on the scalp often become secondarily infected as a result of scratching. The anti-bacterial and anti-fungal properties of beta-ionone reduce the chances of this occurring and when applied frequently to an already infected area represent a moderately effective treatment strategy. Body lice are the group known to be positive primary vectors for bacteria or fungi, however, the anti-bacterial and anti-fungal properties of beta-ionone have prophylactic value in respect of this generally minor risk.

Linalool and Geraniol are both effective pediculocides which have similar properties and similar levels of activity to beta-ionone with which they are synergistic.

Geraniol is also incorporated because of its pediculocidal, anti-bacterial and anti-fungal actions and is mutually synergistic with both beta-ionone and linalool. In addition, geraniol adds a definite and pleasant fragrance.

Eugenol is the active terpene in clove oil. It has topical anaesthetic properties which are valuable in controlling the itching associated with lice and their feeding sites. Eugenol also acts in further synergistic co-operation with beta-ionone, linalool and geraniol in respect of pediculocidal, anti-bacterial and anti-fungal actions. Eugenol also imparts a further distinct fragrance which is pleasantly compatible with that of geraniol.

Myrcene is added mainly for its fragrance properties, however, it does have limited pediculocidal, anti-bacterial and anti-fungal actions.

In preferred embodiments, a mixture of five of the terpenes named above, is blended together briefly—the constituents are readily mutually miscible. Sufficient of the blend is then added to any good quality, conditioning shampoo base, to produce a 4% by volume concentration of the active blended mixture. Such a conditioning shampoo will typically contain water, ammonium lauryl sulfate and ammonium laurethsulfate as a base with palmitic acid or glycol distearate and other ingredients as conditioning agents.

Maximal pediculocidal activity is obtained when the resultant product has a pH is adjusted to between 8 and 8.5, though the exact pH value between these limits is not critical.

The slightly basic shampoo provides the surfactant mechanism needed to enable the terpenes to kill lice at a low level of concentration. Terpenes are non-polar and have no affinity for the exoskeleton of lice. The surfactant effect allows generalised contact of the terpenes with the exoskeleton. Experiments have shown that death of lice results in a few minutes. The same mechanism may be observed in larvae and with egg cases but takes longer and may require an additional application.

Experiments have also led to preliminary observations which suggest that the instant invention softens the adhesive which lice employ to secure eggs to a human hair shaft. When it is required to use a terpene formulation, according to the present invention, as a washing additive, the use of a specific additional surfactant is necessary. I have found that non-ionic, anionic and cationic surfactants all produce satisfactory results but that non-ionic surfactants are markedly superior. In particular, food grade Polysorbate 80, is employed in the preferred embodiments on grounds of efficacy, safety and availability in rank order.

MOST PREFERRED EMBODIMENT

The active ingredients of a formulation for killing lice and eggs which infest humans are blended in the proportions:

| | |
|---|---|
| Redistilled limonene | 45% by volume |
| Beta-ionone | 25% by volume |
| Linalool | 10% by volume |
| Geraniol | 10% by volume |
| Eugenol | 5% by volume |
| Myrcene | 5% by volume |

I most prefer to use a concentration of 4% by volume of this terpene blend in an aqueous shampoo, containing ammonium lauryl sulfate and ammonium laurethsulfate as a base, with palmitic acid or glycol distearate and other minor ingredients as conditioning agents. This concentration is preferred because at this level there is a particularly pleasing gelling effect with the shampoo base, the resulting product is highly pediculocidal and in experiments, there is no evidence of adverse effects on human users. Higher concentrations of the terpene blend are unnecessary and might lead to problems of minor irritation in a small proportion of the population.

Experiments have shown that the formulation, diluted with distilled water to a 2% terpene blend concentration is also pediculocidal. The 2% concentration product may advantageously be used as a spray to kill lice and their eggs on fabrics, including bedding, upholstery and clothing. This product is particularly useful against body lice which, unlike head lice, can survive and live comfortably off a human host and infest fabrics between blood meals.

The 4% formulation, hereinbefore described, may be diluted with distilled water to a 1% terpene blend concentration. This approaches the lowest practicable level and requires significantly increased exposure (dwell time). This would detract from the use of this concentration as a shampoo, since long dwell times are known to be a barrier against user-compliance with prior art shampoos used against lice. However, the 1% concentration may be applied advantageously and in a novel manner as dip solution for the immersion of combs between uses by multiple family members and those in institutionalised groups to prevent cross infection and re-infection. Obviously, immersion times will vary but will generally be extended and sufficient to achieve effectiveness.

The terpene blend of the instant invention may be used in concentrations from about 20% up to 50% as an additive for washing infested fabrics. In this application, the product requires the addition of a surfactant which is optimally the non-ionic surfactant Polysorbate 80 at an overall concentration of up to 10%. The product may be used in either a hot wash (typically 60° C.) or a cold wash (ambient water temperatures). Washing may optionally be carried out in a machine and the process may be an active (agitated) or a passive (steeping) wash.

EXAMPLES

Method of Preparation

In a round bottom flask equipped with a stirring bar are placed redistilled limonene (45.0 gms) beta-ionone (25 0 gms), linalool (10.0 gms), geraniol (10.0 gms), eugenol (5.0 gms), and myrcene (5.0 gms). The resulting mixture is stirred at room temperature for 2 minutes. The flask is then stoppered and the blend stored until required.

In another round bottom flask equipped with a stirring bar is placed 96 gms of a conditioning shampoo containing ammonium lauryl sulfate and ammonium laurethsulfate as a base with palmitic acid or glycol distearate and other minor ingredients as conditioning agents.

To the second flask is added 4 gms of the terpene blend and the contents are stirred slowly at room temperature for about three minutes until gelling is observed to be complete.

The resultant product is then decanted into a screw top container and stored at room temperature until required.

The product is used in the manner of an ordinary conditioning shampoo which is to say that the hair is wetted, the shampoo is applied thoroughly all over the hair and scalp and then left in place for one to two minutes after which it is rinsed off with plenty of warm water.

A spray for the treatment of infested bedding and upholstery is prepared by diluting the shampoo product with distilled water to a concentration of 2% in a suitable flask.

A comb dip is prepared by diluting the shampoo product with distilled water to a concentration of 1% in a suitable flask. The resultant product is stored in a wide mouth, screw top container until required. Additives for use during washing of lice infested fabrics in a washing machine or other vessel are prepared by adding the terpene blend to distilled water to produce a final concentration of 20% to 50% by volume. Sufficient of the non-ionic surfactant Polysorbate 80 is added to produce an overall concentration of 10%.

Use as a Pediculocidal Agent

Experiment 1: Approximately 5 gms of fresh hair croppings from an individual heavily infested with head lice (*Pediculosus humanus capitus*), were placed on a large glass slide and promptly examined under a low power light microscope to confirm the presence of at least ten live lice and ten eggs. Within five minutes of the microscopic examination, the slide and hair cropping were transferred to a shallow glass vessel. Approximately 15 mls of distilled water at about 45° C. was added to the hair croppings which were stirred with a glass rod until the hair was wetted thoroughly. Excess water was then decanted from the vessel and set aside in a small flask. About 2 mls of a shampoo preparation containing 4% of the terpene blend, prepared as described under 'Method of Preparation, above, was added to the wet hair croppings which were turned repeatedly with a glass rod for about 30 seconds to ensure distribution of the shampoo throughout the whole sample, which was then tamped gently for a further 30 seconds to simulate a light scalp message. At the end of this procedure, the hair croppings were transferred to a very fine mesh sieve and subjected to 2 rinses each in separate one liter flasks containing 500 mls of distilled water at about 45° C.

The hair sample was then transferred on to white filter paper and microscopically examined for lice and eggs. Both rinses were filtered and the filter papers microscopically examined for lice and eggs.

No live lice were found. All eggs were non-viable and showed alterations to the casing and reduction in size of the adhesive band attaching them to the hair shaft. A considerable number of eggs were found which were not attached to hair shafts.

Experiment 2: The observation of detachment of eggs from hair shafts seen in Experiment 1, may have occurred due to mechanical manipulation, however, in a parallel experiment, where plain water was used but all other conditions were similar, very few eggs became detached from hair shafts suggesting that action of the active shampoo had been responsible for the detachments observed in Experiment 1 were the shampoo was used.

Experiment 3: A commercially available steel 'nit comb' was used to comb the hair of the heavily infested individual who provided the hair croppings for Experiment 1, at about the same time the hair sample was taken. The comb was placed on a large glass slide and examined with a suitable low power light microscope and the presence of significant numbers of eggs and a few live lice disposed on and between the teeth of the comb was established.

The comb was placed in a wide mouth vessel containing 250 mls of a comb dip prepared as described under 'Method of Preparation' above and left for 30 minutes. At the end of this period the comb was removed gently and allowed to drain over the vessel. It was then placed on a filter paper and examined microscopically. The contents of the wide mouth vessel were then filtered, together with two washings each of 100 mls of tepid distilled water. The filter paper was then examined microscopically. Only dead lice were found together with non-viable eggs.

The product is used at a 1% concentration level as a comb dip to prevent cross infection and re-infection between family members and institutionalised groups.

Experiment 4: A shirt taken from an individual moderately infested with body lice was microscopically examined. A considerable number of live lice and eggs were observed. The shirt was carefully placed in a large polythene bin and sprayed, using a simple plunger mist-spray device filled with a spray liquid prepared as described under 'Method of Preparation' above and left for 30 minutes. About 40 mls were used. At the end of the period, the shirt was once again subjected to careful microscopic examination. Only dead lice and non-viable eggs were found.

Experiment 5: Several items of clothing, including a shirt, trousers and underwear were taken from an individual moderately infested with body lice and microscopically examined. Live lice and eggs were observed in most but not all the items. The clothes were placed carefully in a large polythene bin of 5 gallons capacity containing water at ambient temperature (19° C.), to which 50 mls of a wash additive of 40% concentration, prepared as described under 'Method of Preparation' above had been previously added and stirred in. The aim was to achieve a concentration of the terpene combination in the washing water of at least 0.25%. The clothes were pushed under the surface gently with a polythene rod and left for 1 hour. At the end of the period, the shirt was removed from the bin, compressed gently to remove most of the water and then once again subjected to careful microscopic examination. Only dead lice and non-viable eggs were found.

Experiment 6: Several items of clothing, including a shirt, trousers and underwear were taken from an microscopically examined. Live lice and eggs were observed in most but not all the items. The clothes were placed carefully in a washing machine to which 50 mls of a wash additive of 20% concentration, prepared as described under 'Method of Preparation' above had been previously added. The aim was to achieve a concentration of the terpene combination in the washing water of at least 0.25%. In addition, the normal manufacturer's specified amount of domestic detergent was added, appropriate to the cycle and load. The washing machine was set to a standard agitating wash cycle involving rinse and spin stages and having a maximum temperature of 50° C. and a duration of 41 minutes. At the end of the cycle, the clothes were once again subjected to careful microscopic examination. No lice and only a few non-viable eggs were found.

In a control experiment using a similar batch of clothes washed in the same machine on the same cycle but without the laundry additive of the instant invention, no live lice were found but some eggs were found after the wash cycle still adhering to seams. A small number of these were thought possibly to be viable.

The method of preparation and experiments in the uses of the instant invention and quoted by way of example only and it will be evident to those skilled in the art that single terpenes and other combinations of terpenes employing some or all the terpenes described as well as other methods of preparation, concentrations and numerous other uses may be derived without departing from the scope and spirit of the invention.

I claim:

1. An insecticide to exterminate lice and lice eggs comprising:
    as active ingredient of the insecticide a pediculicidally effective amount of a mixture of the terpene compounds redistilled limonene, beta-ionone, linalool, geraniol, eugenol and myrcene, wherein the terpene compounds are diluted in an aqueous solution.

2. The insecticide of claim 1, said insecticide comprising the following terpene components in percent by volume given with respect to the active ingredient of the insecticide:
    redistilled limonene 45%;
    beta-ionone 25%;
    linalool 10%;
    geraniol 10%;
    eugenol 5%; and
    myrcene 5%.

3. The insecticide of claim 2 having a concentration ranging from 1% to 50% by volume of said active ingredient.

4. The insecticide of claim 3, wherein said aqueous solution includes distilled water.

5. The insecticide of claim 3 having a concentration of 4% by volume of said active ingredient.

6. The insecticide of claim 3 having a pH ranging from between 8 and 8.5.

7. The insecticide of claim 1, wherein said aqueous solution includes a shampoo base for application to human hair.

8. The insecticide of claim 1, wherein said aqueous solution includes ammonium lauryl sulfate and ammonium laurethsulfate.

9. The insecticide of claim 1 or 8, wherein said aqueous solution includes one or more hair conditioning agents.

10. The insecticide of claim 9, wherein said one or more hair conditioning agents include one or both of palmitic acid or glycol distearate.

11. The insecticide of claim 1, wherein said aqueous solution is in the form of a spray for use on fabrics.

12. The insecticide of claim 1, wherein said aqueous solution is in the form of a dipping solution for the immersion of combs.

13. The insecticide of claim 1, wherein said aqueous solution is in the form of an additive for the washing of laundry.

14. The insecticide of claim 1, wherein the aqueous solution contains a surfactant.

15. The insecticide of claim 14, wherein said surfactant is non-ionic.

16. The insecticide of claim 15, wherein said non-ionic surfactant is Polysorbate 80.

17. A method for manufacturing an insecticide for exterminating lice and lice eggs comprising the step of mixing as active ingredient of the insecticide a pediculicidally effective amount of the terpene compounds redistilled limonene, beta-ionone, linalool, geraniol, eugenol and myrcene in an aqueous solution of distilled water.

18. The method of claim 17, wherein said step of mixing said terpene compounds in the aqueous solution of distilled water comprises mixing said terpene compounds in the following percentages by volume of the active ingredient of said insecticide:
    redistilled limonene 45%;
    beta-ionone 25%;
    linalool 10%;
    geraniol 10%;
    eugenol 5%; and
    myrcene 5%.

19. The method of claim 18, wherein said step of mixing said terpene compounds in the aqueous solution includes forming a concentration of said active ingredient ranging from 1% to 50% by volume.

20. The method of claim 19, wherein in said step of mixing said terpene compounds in the aqueous solution, the concentration of said active ingredient is 4% by volume.

21. The method of claim 17, further comprising the step of adding shampoo base elements.

22. The method of claim 21, wherein in the step of adding shampoo base elements, said shampoo base elements include ammonium lauryl sulfate and ammonium laurethsulfate.

23. The method of claim 21, further comprising the step of adding hair conditioning agents.

24. The method of claim 23, wherein in the step of adding hair conditioning agents, said conditioning agents include one or both of palmitic acid or glycol distearate.

25. The method of claim 17, further comprising the step of adding surfactant to said aqueous solution.

26. The method of claim 25, wherein in the step of adding surfactant to said aqueous solution, the surfactant is Polysorbate 80.

* * * * *